United States Patent [19]

Fritch et al.

[11] Patent Number: 4,954,652
[45] Date of Patent: Sep. 4, 1990

[54] PRODUCTION OF ACETAMINOPHEN

[75] Inventors: John R. Fritch; Olan S Fruchey; Theodore Horlenko, all of Corpus Christi, Tex.

[73] Assignee: Hoechst Celanese Corporation, Somerville, N.J.

[21] Appl. No.: 217,652

[22] Filed: Jul. 12, 1988

[51] Int. Cl.$^5$ ............... C07C 231/05; C07C 233/42; C07C 235/12; C07C 235/16
[52] U.S. Cl. ................................ 564/223; 564/305
[58] Field of Search ........................ 564/305, 223

[56] References Cited

U.S. PATENT DOCUMENTS 4,524,217  6/1985  Davenport et al. ............ 564/223
4,560,789  12/1985 Davenport et al. ............ 560/142
4,568,763  2/1986  Davenport et al. ............ 560/142

FOREIGN PATENT DOCUMENTS 0168908  1/1986  European Pat. Off. .

Primary Examiner—John Kight, III
Assistant Examiner—C. Azpuru
Attorney, Agent, or Firm—D. R. Cassady

[57] ABSTRACT

N-acetyl-para-aminophenol is prepared by subjecting 4-hydroxyacetophenone oxime to a Beckmann rearrangement in the presence of a thionyl chloride catalyst and an alkyl alkanoate as the reaction solvent. An integrated process is disclosed wherein 4-hydroxyacetophenone is reacted with a hydroxyl amine salt and a base to obtain the ketoxime of the ketone, e.g., 4-hydroxyacetophenone oxime, extracting the ketoxime product from the reaction with alkanoate ester and subjecting the ketoxime dissolved in the ester to a Beckmann rearrangement in the presence of a thionyl chloride catalyst.

16 Claims, No Drawings

PRODUCTION OF ACETAMINOPHEN

This invention relates to a novel process for the production of N-acetyl-para-aminophenol (APAP) by the Beckmann rearrangement of 4-hydroxyacetophenone oxime using an acid catalyst. The invention is also concerned with an integrated process for preparing APAP by first producing 4-hydroxyacetophenone oxime from 4-hydroxyacetophenone (4-HAP), extracting the oxime from the reaction mixture with a solvent, and proceeding with the acid catalyzed Beckmann rearrangement of 4-hydroxyacetophenone oxime in the solvent used to extract the oxime.

BACKGROUND OF THE INVENTION

It is known to prepare N-acyl-hydroxy aromatic amines, e.g., N-acetyl-para-aminophenol (APAP), by acetylating the corresponding hydroxy aromatic amine, e.g. para-aminophenol, with an acetylating agent such as an anhydride, e.g., acetic anhydride. However, this reaction may cause problems such as the difficulty of mono-acetylating the amine group, oligomerization of the hydroxy aromatic amine, and color body formation. Nonetheless, the APAP made by this reaction is an important commodity of commerce, being one of the most widely used over-the-counter analgesics.

In U.S. Pat. No. 4,524,217 there is disclosed a novel process for the preparation of N-acyl-hydroxy aromatic amines, in general, and N-acetyl-para-aminophenol (APAP), in particular. The APAP is formed by a two-step process in which the first step involves reacting 4-hydroxyacetophenone (4-HAP) with a hydroxylamine salt in a base to obtain the ketoxime of the ketone (4-HAP oxime), and then subjecting the ketoxime to a Beckmann rearrangement in the presence of a catalyst to form APAP. Although various materials can be used as the Beckmann rearrangement catalyst, U.S. Pat. No. 4,524,217 discloses preferred use of thionyl chloride in liquid sulfur dioxide. The entire content of U.S. Pat. No. 4,524,217 is herein incorporated by reference.

Although sulfur dioxide has been found to be an excellent solvent for the Beckmann rearrangement of 4-HAP oxime to APAP or acetaminophen, there are certain characteristics of sulfur dioxide which are disadvantageous. For one, $SO_2$ is toxic. Accordingly, extraordinary precautions must be taken to handle and contain the sulfur dioxide and such precautions obviously require specialized equipment. For example, centrifuges do not adequately contain sulfur dioxide and therefore cannot be used for separation of the crude solid APAP product from the sulfur dioxide reaction liquor. Consequently, such separation must be accomplished by filtration with equipment that is more expensive to purchase and operate than a centrifuge. Furthermore, centrifugation is inherently suited for continuous processing, whereas filtration is not. Additionally, $SO_2$ is corrosive and requires expensive metallurgy. Use of $SO_2$ as solvent may also lead to the formation of metallic contaminants from the processing equipment. Such contaminants may affect reaction rates and/or lead to the formation of by-products. Obviously, since APAP is an analgesic for human consumption, the product should be as pure as possible, and, thus, minute impurities from corrosion products are definitely not desirable. Removal of corrosion products from the APAP adds to the operating costs. Moreover, the $SO_2$ must be pressurized for use in the liquid state. Added costs for pressurized equipment and operating are the result.

Another disadvantage with the prior two-step process of producing APAP from 4-HAP by first forming the 4-HAP oxime and then subjecting the oxime to Beckmann rearrangement with thionyl chloride in $SO_2$ is that the oxime is prepared in water and must be recovered by chilling the aqueous oximation product to crystallize the oxime. The crystallized oxime must then be collected and dried prior to Beckmann rearrangement. The dried oxime is then fed to the APAP reactor via a hopper system. This arrangement requires solids crystallization, collection, drying, storage, and handling and the consequent use of additional and expensive equipment.

Accordingly, it would be advantageous to provide an alternative solvent to $SO_2$ for use in the Beckmann rearrangement of 4-HAP oxime to APAP. Such a solvent should be less toxic, less volatile, and less corrosive than $SO_2$. The solvent must also provide good yields of APAP and provide for the formation of a pure APAP product. It is therefore the primary objective of the present invention to provide an alternative solvent to $SO_2$ in the above-described Beckmann rearrangement reaction, which solvent is less toxic, less volatile, and less corrosive, and which reduces capital costs and can greatly reduce the handling and operating costs of the two step process of forming APAP from 4-hydroxyacetophenone.

SUMMARY OF THE INVENTION

In accordance with the present invention, alkyl alkanoate esters are used as the solvent for the Beckmann rearrangement of 4-hydroxyacetophenone oxime (4-HAP oxime) to acetaminophen (APAP). The Beckmann rearrangement utilizes an acid catalyst such as thionyl chloride. The Beckmann rearrangement may be carried out in the presence of potassium iodide which serves to minimize the formation of by-products which contaminate the APAP product.

An important advantage of utilizing alkyl alkanoate esters as the solvent for the Beckmann rearrangement of 4-HAP oxime to APAP is that alkyl alkanoate esters can be utilized to extract the 4-HAP oxime from the aqueous product which is formed from the reaction of 4-HAP with hydroxylamine in the first step of the integrated process. After removal of water, preferably by azeotropic distillation, the extracted 4-HAP oxime and alkyl alkanoate ester mixture can be fed to the reactor used in the Beckmann rearrangement.

DETAILED DESCRIPTION OF THE INVENTION

In accordance with this invention, N-acetyl-paraaminophenol (APAP) is produced by reacting 4-hydroxyacetophenone (4-HAP) with a hydroxylamine salt to form the ketoxime of the ketone and subjecting the ketoxime to a Beckmann rearrangement in the presence of an acid catalyst such as thionyl chloride to form the N-acyl-hydroxyaromatic amine.

The ketoxime formation proceeds as in equation (I):

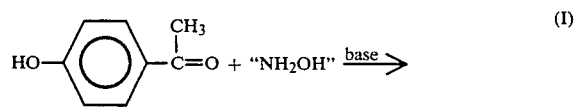

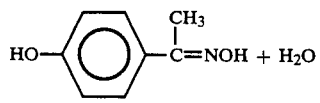

The Beckmann rearrangement to form the desired APAP product proceeds as in equation (II):

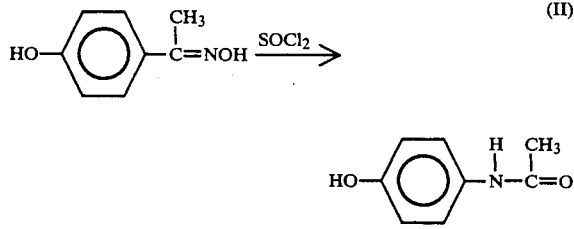

4-Hydroxyacetophenone used to form the oxime may be prepared by any method known in the art. For example, it may be prepared by the Fries rearrangement of phenyl acetate or, alternatively, in a Friedel-Crafts acetylation of phenol. The catalyst for both mentioned reactions is preferably hydrogen fluoride, but any other catalyst known in the art to be effective for the Fries or Friedel-Crafts reactions may be used, e.g., aluminum chloride, zinc chloride or boron trifluoride. A more detailed description of methods of forming the hydroxyaromatic ketone are described in the aforementioned U.S. Pat. No. 4,524,217.

The conversion of 4-HAP into the ketoxime by equation (I) is accomplished by contacting the ketone with a hydroxylamine salt, e.g., hydroxylamine hydrochloride, hydroxylamine sulfate, hydroxylamine bisulfate, or hydroxylamine phosphate, and a base, e.g. ammonium hydroxide (aqueous ammonia), potassium hydroxide, sodium hydroxide, or lithium hydroxide. Since hydroxylamine is sensitive and decomposes in its free form, it is commercially supplied as its acid salt. The free hydroxylamine is liberated upon treatment of the acid salt with the base. If sodium hydroxide or aqueous ammonia is used as the base to liberate hydroxylamine from its acidic sulfate salt, then such liberation also produces sodium or ammonium sulfate, respectively, as a by-product. In the integrated process for producing APAP from 4-HAP (disclosed in detail below) wherein the oxime is directed to the Beckmann rearrangement reactor in a liquid extraction solvent, it is preferred to use a strong base such as the alkali metal hydroxides to liberate the hydroxylamine.

The base should be used in an amount, for example, of 0.5 to 2 molar equivalents per molar equivalent of starting hydroxylamine. The base is preferably used in an amount of 0.8–1.0 molar equivalents per molar equivalent of starting hydroxylamine so that a small amount of hydroxylamine remains in the form of its acid salt to create a pH buffer that maintains the pH of the oximation reaction in the range of 3–7. Use of larger amounts of base can cause the pH to rise above 7 and result in initiating undesirable condensation reactions of 4-HAP and its oxime. The hydroxylamine acid salt is preferably used in an amount of 1-2 molar equivalents of starting hydroxylamine per mole of starting 4-HAP. Oximation is run at a temperature, for example of 0° to 200° C., for a period of from about 5 minutes to 4 hours. Any pressure may be used, e.g., 80 mm of mercury to 20 atmospheres absolute. The reaction is preferably carried out in an aqueous or alcoholic medium, i.e., in the presence of water and/or an alcohol such as methanol, ethanol, or isopropanol.

The 4-HAP oxime is converted into APAP by a Beckmann rearrangement as shown in equation (II), by contacting the ketoxime with an acid catalyst such as thionyl chloride at a reaction temperature, for example of from 0° to 100° C. for a period of from about 5 minutes to 4 hours. The pressure is not critical and may be, for example, in the range of 1 mm of mercury to 10 atmospheres absolute. The Beckmann rearrangement can be carried out quite successfully with large amounts of undissolved 4-HAP oxime solids and large amounts of undissolved APAP solids suspended in the reaction mixture. The amount of reaction solvent should be sufficiently large so that any undissolved solids form a slurry that settles under the force of gravity and is stirrable, but should not be so large as to prevent crystallization of the APAP product when the reaction mixture is chilled. Thus, the reaction solvent should be present in amounts of from about 0.75–50:1 by weight with respect to the 4-HAP oxime. The weight ratio of oxime to thionyl chloride ranges from about 5:1 up to about 300:1.

The process of this invention is preferably carried out by adding an alkali metal iodide such as potassium iodide to the 4-hydroxyacetophenone oxime prior to carrying out the Beckmann rearrangement in thionyl chloride and alkyl alkanoate ester. Potassium iodide serves to minimize formation of by-products that can contaminate the APAP product. The amount of metal iodide utilized is extremely small and very acceptable results have been obtained when using 0.2 wt. % of potassium iodide relative to the oxime. It should be realized that no particular advantage is gained in going over the 0.2 gram per 100 grams of 4-hydroxyacetophenone oxime but, obviously, such can be done if desired. The amount of inorganic iodide which should be added is that amount sufficient to substantially prevent the formation of chlorinated by-products and said amount is usually in the range varying from about 0.02 gram to about 2.0 grams of potassium iodide per 100 grams of 4-hydroxyacetophenone oxime which is subjected to the Beckmann rearrangement.

The manner in which iodide is added to the Beckmann rearrangement reactor is by no means critical. Iodide can be added directly to the reactor or can be contained in a recycle stream of the reaction mixture solvent. A more detailed description of potassium iodide addition to the Beckmann rearrangement reactor is given in commonly assigned, copending application U.S. Ser. No. 118,117, filed Nov. 6, 1987, herein incorporated by reference, now allowed Feb. 17, 1989.

The use of alkyl alkanoate esters as the Beckmann rearrangement solvent is advantageous inasmuch as the Beckmann rearrangement can now be carried out continuously or batchwise with a centrifuge rather than batchwise with a Rosemund filter which was required utilizing $SO_2$ as the solvent. Alkyl alkanoate esters are much less volatile, less toxic, and less corrosive than sulfur dioxide and therefore avoid the previously described disadvantages of sulfur dioxide. Another important advantage of utilizing an alkyl alkanoate ester as the solvent is that the crystallization, isolation, drying, handling, and storage of solid 4-HAP oxime can be eliminated by extracting 4-HAP oxime directly from the oximation product stream with the alkyl alkanoate ester, removing water from the resulting alkyl alkanoate ester solution of oxime, and charging the Beckmann rearrangement reactor with the dry solution of oxime dissolved in the alkyl alkanoate ester.

Although extraction of 4-HAP oxime with an alkyl alkanoate ester extraction solvent is preferably carried out on hot oximation product to prevent crystallization of 4-HAP oxime and to avoid the expense of a cooling step, the extraction can also be carried out on a chilled aqueous oximation product in which the 4-HAP oxime product has crystallized. In either case, mixing of the alkyl alkanoate ester extraction solvent with the aqueous oximation product yields two liquid phases: an upper liquid organic phase comprising the alkyl alkanoate ester and 4-HAP oxime, and a lower aqueous phase comprising water and the salt which is formed during liberation of the hydroxylamine. The preferred weight ratio of extraction solvent to 4-HAP oxime product is about 0.5-5:1. The aqueous phase thus obtained is preferably extracted with the alkyl alkanoate ester extraction solvent at least one more time to recover additional 4-HAP oxime. Alternatively, the extraction of aqueous oximation product with alkyl alkanoate ester extraction solvent may be carried out continuously in a York-Scheibel countercurrent-type extractor.

The upper liquid organic phases are dried, preferably by distillative removal of water as an azeotrope with the alkyl alkanoate ester extraction solvent. The distillation residue, which comprises a dry alkyl alkanoate ester extraction solvent solution of 4-HAP oxime, can then be fed directly into the Beckmann rearrangement reactor.

If the oxime is to be extracted with an alkyl alkanoate ester, it has been found that the use of a strong base such as sodium hydroxide has an important advantage over relatively weak bases such as ammonium hydroxide (aqueous ammonia) in the first stage of the process wherein is provided the liberation of free hydroxylamine from a corresponding acid salt such as hydroxylammonium sulfate. The disadvantage of weak bases such as ammonium hydroxide is that their use causes rearrangement of 4-HAP oxime to acetaminophen and hydrolysis of acetaminophen and 4-HAP oxime to p-aminophenol and 4-HAP, respectively, during the distillative drying of the extracted oxime. Traces of the acid salt corresponding to the weak base, for example, ammonium sulfate, presumably catalyze these undesirable side reactions during the distillative drying step. Furthermore, previously useful purification techniques failed to give an acceptable acetaminophen product when a relatively weak base such as ammonium hydroxide was used to liberate free hydroxylamine. Use of strong bases such as sodium hydroxide avoids the undesirable side reactions and permits successful purification of the crude acetaminophen product by previously disclosed methods. The by-products produced with a strong base, for example, sodium sulfate and water from sodium hydroxide, apparently do not catalyze undesirable reactions during the distillative drying step.

The reaction solvent used in this invention is, as previously discussed, an alkyl ester of an alkanoic acid. Preferably the alkylester group has 1 to 6 carbon atoms and the alkanoic acid contains 2 to 6 carbon atoms. Specific nonlimiting examples of alkyl alkanoate esters that have proven useful in the present invention include ethyl acetate, butyl acetate, methyl n-hexanoate, and n-hexyl acetate. A preferred solvent is made from alkyl esters of acetic acid. Acetate esters have the advantage of rendering degenerate any possible alkanoate exchange between the alkyl alkanoate ester and the N-acetyl-p-aminophenol product.

Subsequent to the recovery of the product of the Beckmann rearrangement, the ester solvent can be recycled to either the Beckmann rearrangement or to the oxime extraction.

The invention will be further illustrated by the following nonlimiting examples.

EXAMPLE 1

A slurry of 4-HAP oxime (100.00 g, 0.6617 mols) and potassium iodide (0.200 g) in ethyl acetate (185 mL) is stirred and heated to 50° C. under nitrogen (290 torr absolute total pressure). A solution of thionyl chloride (1.0 mL, 1.631 g, 13.71 mmole) in ethyl acetate (15 mL) is then added over 25 minutes to the stirred 4-HAP oxime/ethyl acetate slurry. The temperature of the reaction mixture is maintained at 50°-51° C. by allowing the heat of reaction to reflux the ethyl acetate solvent under 290 torr absolute total pressure. Within about ten minutes after the start of the thionyl chloride addition, the reaction mixture is a nearly homogeneous, light amber liquid. White solid APAP then begins to precipitate. The refluxing starts to subside after about 90% of the thionyl chloride has been added. After the thionyl chloride addition is completed, the reaction mixture is allowed to cool to 40° C. over about ten minutes and is then chilled in an ice bath to 3° C. The reaction slurry is filtered under nitrogen to give a cake of light yellow Beckmann reaction solids and a filtrate of yellow Beckmann reaction liquor. Residual ethyl acetate is pumped off the reaction solids at 0.025 torr and ambient temperature. The dried reaction solids are then purified by known washing, filtering and recrystallization procedures. Results are shown in Table 1. The solid filter material used in the purification is dried under vacuum (0.025 torr) at ambient temperature to a mass 3.53 g greater than the weight of the starting filter material; this mass increase presumably is due mostly to adsorbed APAP. Throughout the entire preparation, the crude APAP solids and purified APAP solids are granular, free of tackiness, and easily handled.

EXAMPLE 2

The preparation of Example 1 is repeated with the starting 4-HAP oxime/ethyl acetate slurry containing 90 mL instead of 185 mL of ethyl acetate. Under these conditions, the reaction mixture contains substantial amounts of white solid throughout the entire reaction period. As the refluxing subsides near completion of the thionyl chloride addition, the reaction slurry becomes so viscous that it no longer settles under the force of gravity. Throughout the entire preparation, the crude APAP solids and purified APAP solids are granular, free of tackiness, and easily handled. Results are shown in Table 1.

EXAMPLE 3

The preparation of Example 1 is repeated with the starting 4-HAP oxime/ethyl acetate slurry containing 475 mL instead of 185 mL of ethyl acetate. This volume of ethyl acetate is sufficient to dissolve essentially all of the starting 4-HAP oxime at 25° C. The reaction mixture remains essentially homogeneous until about one-third of the thionyl chloride catalyst has been added, at which time the APAP product starts to precipitate as a white solid. Throughout the entire preparation, the crude APAP solids and purified APAP solids are granular, free of tackiness, and easily handled. Results are shown in Table 1.

EXAMPLE 4

The preparation of Example 1 is repeated without KI. The crude and purified APAP products are noticeably more colored than their counterparts from Example 1. Throughout the entire preparation, the crude APAP solids and purified APAP solids are granular, free of tackiness, and easily handled. Results are shown in Table 1.

EXAMPLE 5

The preparation of Example 1 is repeated with the Beckmann reaction being run at 32° C. under 150 torr absolute total pressure. Throughout the entire preparation, the crude APAP solids and purified APAP solids are granular, free of tackiness, and easily handled. Results are shown in Table 1.

EXAMPLE 6

The preparation of Example 1 is repeated with the following modifications. In the starting 4-HAP oxime/ethyl acetate slurry, the ethyl acetate Beckmann reaction liquor from the preparation of Example 1 is used in place of 185 mL of fresh ethyl acetate. The catalyst solution consists of thionyl chloride (1.3 mL instead of 1.0 mL) in fresh ethyl acetate (50 mL instead of 15 mL to make up the ethyl acetate loss in the drying step of Example 1). Fresh, acid-washed activated carbon (0.500 g) is now also included with the starting 4-HAP oxime/ethyl acetate slurry. The dried reaction solids are purified by known methods. Throughout the entire preparation, the crude APAP solids and purified APAP solids are granular, free of tackiness, and easily handled. Results are shown in Table 1.

EXAMPLE 7

To a stirred solution of 4-HAP (100.00 g) and hydroxylamine sulfate (63.6 g) in water (370 mL) heated to 80° C. is added a solution of sodium hydroxide (30.5 g) in water (100 mL) over five minutes. The stirred, homogeneous, yellow reaction mixture is refluxed at 102°–103° C. under air for 20 minutes and then cooled to 25° C. Ethyl acetate (200 mL) is then added to the cooled reaction mixture, which contains a large amount of crystallized 4-HAP oxime. The three-phase mixture is shaken well for about half a minute and then allowed to settle. Two liquid phases separate completely within about one minute, leaving only a small amount of undissolved solid. The bottom aqueous phase and the undissolved solids are separated from the upper ethyl acetate phase and then extracted with two or more 100 mL portions of ethyl acetate.

The three ethyl acetate extracts are combined and dried by azeotropic distillation under nitrogen at atmospheric pressure in two steps. The first step, which employs a Dean-Stark trap under conditions of total reflux, removes 34.5 mL of aqueous phase distillate. The second step, which employs a 10-tray Oldershaw column and a reflux to takeoff ratio of 3:1, yields 200 mL of cloudy distillate and a stable final overhead temperature of 77.1° C. The distillates are found by analysis to contain less than 0.02 wt % each of acetic acid and ethanol.

On cooling, 4-HAP oxime crystallizes from the amber distillation residue. The resulting dry slurry of 4-HAP oxime in ethyl acetate is then subjected to the conditions of the Beckmann rearrangement described in Example 1 using 0.200 g of KI, 85 mL of fresh additional ethyl acetate, and a catalyst solution of thionyl chloride (1.3 mL) in ethyl acetate (15 mL). The APAP product is recovered, recrystallized, and washed. Throughout the entire preparation, the crude APAP solids and purified APAP solids are granular, free of tackiness, and easily handled. Results are shown in Table 1.

EXAMPLE 8

The oximation/Beckmann reaction sequence of Example 7 is repeated with only one significant modification now described. The aqueous reaction mixture from the oximation reaction is drained hot (about 100° C.) over five minutes into a round bottom flask containing ethyl acetate (200 mL) and equipped with a reflux condenser. The ethyl acetate refluxes very gently under atmospheric pressure for only a short period during the addition. When the addition is complete, the mixture is at about 73° C. and is mixed well by stirring vigorously for about one minute. Two homogeneous liquid phases then separate completely within about one minute leaving no undissolved solids. The lower (aqueous) phase is extracted with two more 100 mL portions of ethyl acetate as described in Example 7.

The distillates from the axeotropic drying steps are found by analysis to contain less than 0.02 wt % each of ethanol and acetic acid. Throughout the entire preparation, the crude APAP solids and purified APAP solids are granular, free of tackiness, and easily handled. Results are shown in Table 1.

EXAMPLE 9

The oximation/Beckmann rearrangement reaction sequence of Example 7 is repeated with 29 wt % aqueous ammonia (60 mL) being used instead of aqueous sodium hydroxide as the base to liberate free hydroxylamine during the oximation. Results are shown in Table 1.

EXAMPLE 10

The oximation/Beckmann rearrangement sequence of Example 8 is repeated with the following modifications. Instead of 370 mL of fresh water, the oximation uses 148 mL of fresh water and 222 mL of the aqueous phase remaining after extraction of the oximation product of Example 8 with ethyl acetate. Instead of being drained into 200 mL of fresh ethyl acetate, the hot oximation product is drained into the ethyl acetate Beckmann reaction liquor recovered from the preparation of Example 8. Extraction of the oximation product is then completed with two 100 mL portions of the wet ethyl acetate distilled off the ethyl acetate extracts of Example 8. For the Beckmann rearrangement, the ethyl acetate solution of thionyl chloride uses 50 mL of fresh ethyl acetate instead of 15 mL to make up the ethyl acetate loss in the drying step of Example 8. Fresh, acid-washed activated carbon (0.500 g) is now also included with the starting 4-HAP oxime/ethyl acetate slurry. After removal of residual ethyl acetate, the dried reaction solids are purified by known methods.

The distillates from the azeotropic drying steps are found by analysis to contain no more than 0.032 wt. % each of ethanol and acetic acid. Throughout the entire preparation, the crude APAP solids and purified APAP solids are granular, free of tackiness, and easily handled. Results are shown in Table 1.

EXAMPLE 11

A slurry of 4-HAP oxime (100.00 grams, 0.6617 moles) in n-hexyl acetate (450 mL) containing no potassium iodide is stirred and heated to 60° C. under nitrogen (8 torr absolute total pressure). A solution of thionyl chloride (1.3 mL, 2.120 grams, 17.82 mmole) in hexyl acetate (50 mL) is then added over 30 minutes to the stirred 4-HAP oxime/hexyl acetate slurry. The temperature of the reaction mixture is maintained at 58°–65° C. by allowing the heat of reaction to reflux the hexyl acetate solvent under 8 torr absolute total pressure. Within about five minutes after the start of the thionyl chloride addition, the reaction mixture is a nearly homogeneous amber liquid. Pale yellow solid APAP then precipitates during the remainder of the thionyl chloride addition. The refluxing starts to subside after about 90% of the thionyl chloride has been added. After the thionyl chloride addition is completed, the reaction mixture is chilled in an ice bath to 5° C. The reaction slurry is filtered under nitrogen to give a cake of golden yellow Beckmann reaction solids and a filtrate of yellow Beckmann reaction liquor. Residual hexyl acetate is pumped off the reaction solids at 0.025 torr and ambient temperature. The dried reaction solids are then purified by known washing, filtration, and recrystallization procedures. The results shown in Table 1 do not include 2.85 g of 98.8% pure APAP that precipitates from the yellow Beckmann reaction liquor on standing overnight at room temperature under air. Throughout the entire preparation, the crude APAP solids and purified APAP solids are granular and handled without problem.

EXAMPLE 12

The preparation of Example 11 is repeated at 50° C. and 17 torr total absolute pressure with methyl n-hexanoate instead n-hexyl acetate as the reaction solvent. Throughout the entire preparation, the crude APAP solids and purified APAP solids are granular and handled without problem. Results are shown in Table 1.

TABLE 1

| | Example No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 4-HAP Oxime Conversion (%) | 99.44 | 98.94 | 99.51 | 97.56 | 97.22 | 98.94 | 99.64 | 99.24 | 97.18 | 99.49 | 98.94 | 92.48 |
| Product Efficiencies (%) | | | | | | | | | | | | |
| APAP | 98.52 | 98.98 | 99.01 | 98.78 | 98.97 | 97.95 | 97.52 | 97.21 | 83.75 | 98.01 | 96.81 | 96.09 |
| 4-HAP | 1.12 | 0.61 | 0.54 | 0.66 | 0.22 | 1.85 | 2.03 | 2.09 | 3.19 | 1.71 | 2.35 | 3.21 |
| Other By-Products | 0.36 | 0.41 | 0.46 | 0.56 | 0.81 | 0.19 | 0.45 | 0.70 | 13.06[1] | 0.29 | 0.84 | 0.69 |
| Yield of Purified APAP (%) | 75.75 | | | 75.91 | | 79.94 | 73.66 | | | 75.10 | 56.03 | 54.00 |
| Analysis of Purified APAP | | | | | | | | | | | | |
| 4-HAP (wt %) | 0.009 | | | 0.015 | | 0.020 | 0.017 | | | 0.000 | 0.002 | 0.000 |
| 4-HAP Oxime (wt %) | 0.001 | | | 0.000 | | 0.000 | 0.000 | | | 0.000 | 0.000 | 0.000 |
| Other Impurities (wt %) | 0.015 | | | 0.060 | | 0.020 | 0.147 | | | 0.015 | 0.042 | 0.013 |
| Limit of Color[2] | 0.011 | | | 0.038 | | 0.008 | 0.030 | | | 0.025 | 0.048 | 0.053 |

[1]Most of this figure (12.47%) is due to p-aminophenol.
[2]Limit of Color is the 420 nm absorbance of the supernate obtained from centrifugation of a slurry of 10 g of solid sample in 10 mL of methanol.

What is claimed is:

1. A process for the production of N-acetyl-para-aminophenol from 4-hydroxyacetophenone comprising reacting said 4-hydroxyacetophenone with hydroxylamine under conditions to form an aqueous solution of 4-hydroxyacetophenone oxime, extracting the oxime from said aqueous solution with an alkyl alkanoate ester to form a mixture of said oxime dissolved in said alkyl alkanoate ester, contacting said mixture with a Beckmann rearrangement catalyst to form said N-acetyl-para-aminophenol product and recovering said product from the alkyl alkanoate ester.

2. The process of claim 1, wherein said oxime is formed by contacting 4-hydroxyacetophenone with a hydroxylamine salt and a base.

3. The process of claim 2, wherein said base is selected from the group consisting of ammonium hydroxide and alkali metal hydroxides.

4. The process of claim 3, wherein said base is an alkali metal hydroxide.

5. The process of claim 4, wherein said alkali metal hydroxide is sodium hydroxide.

6. The process of claim 1, wherein the mixture of alkyl alkanoate ester and oxime is distilled to remove water prior to said Beckmann rearrangement.

7. The process of claim 1, wherein the catalyst for said Beckmann rearrangement is thionyl chloride.

8. The process of claim 1, wherein said Beckmann rearrangement is run under an inert atmosphere at total pressures of from 1 mm Hg to 10 atmospheres absolute.

9. The process of claim 8, wherein said Beckmann rearrangement is run under a vacuum.

10. The process of claim 8, wherein said Beckmann rearrangement is run under nitrogen.

11. The process of claim 1, wherein said alkanoate ester is formed from an alkyl group containing 1 to 6 carbon atoms and from a $C_2$–$C_6$ alkanoic acid.

12. The process of claim 11, wherein said ester is ethyl acetate.

13. The process of claim 11, wherein said ester is butyl acetate.

14. The process of claim 1, wherein said Beckmann rearrangement and recovery of said product are run continuously.

15. The process of claim 14, wherein subsequent to recovery of said product, recycling said ester to the Beckmann rearrangement.

16. The process of claim 14, wherein subsequent to recovery of said product, recycling said ester to oxime extraction.

* * * * *